United States Patent [19]

Chatman, Jr. et al.

[11] Patent Number: 5,378,225
[45] Date of Patent: Jan. 3, 1995

[54] HEATED BACK SUPPORT

[76] Inventors: Jules Chatman, Jr.; Cynthia A. Chatman, both of 877 Stanford Ave., Oakland, Calif. 94608

[21] Appl. No.: 149,518
[22] Filed: Nov. 9, 1993
[51] Int. Cl.⁶ .............................................. A61F 5/02
[52] U.S. Cl. ...................................... 602/19; 607/108; 607/112; 601/15; 601/49
[58] Field of Search ..................... 602/14, 19; 607/108, 607/112; 128/32, 48, 51, 52, 36, 41

[56] References Cited

U.S. PATENT DOCUMENTS

| | | | |
|---|---|---|---|
| 1,594,053 | 7/1926 | Evans | 607/112 X |
| 1,736,590 | 11/1929 | Graham et al. | 607/112 X |
| 2,584,302 | 2/1952 | Stein | 607/108 X |
| 2,590,212 | 3/1952 | Samuels | 607/112 X |
| 3,407,818 | 10/1968 | Costanzo | 607/108 |
| 4,475,543 | 10/1984 | Brooks et al. | 602/19 |
| 4,702,235 | 10/1987 | Hong | 607/108 X |
| 5,179,942 | 1/1993 | Drulias et al. | 602/19 X |

Primary Examiner—Richard J. Apley
Assistant Examiner—Beverly A. Meindl
Attorney, Agent, or Firm—Hugh E. Smith

[57] ABSTRACT

A heated back support comprising an elongated strap having a securement means at one end and a securable means at the other end, the strap adapted to be worn around a user's body, a plurality of heating elements coupled to the strap such that the elements are positionable adjacent to a user's back, a power source, and a switch means coupled to the power source and heating elements for selectively energizing the elements to heat a user's back.

2 Claims, 4 Drawing Sheets

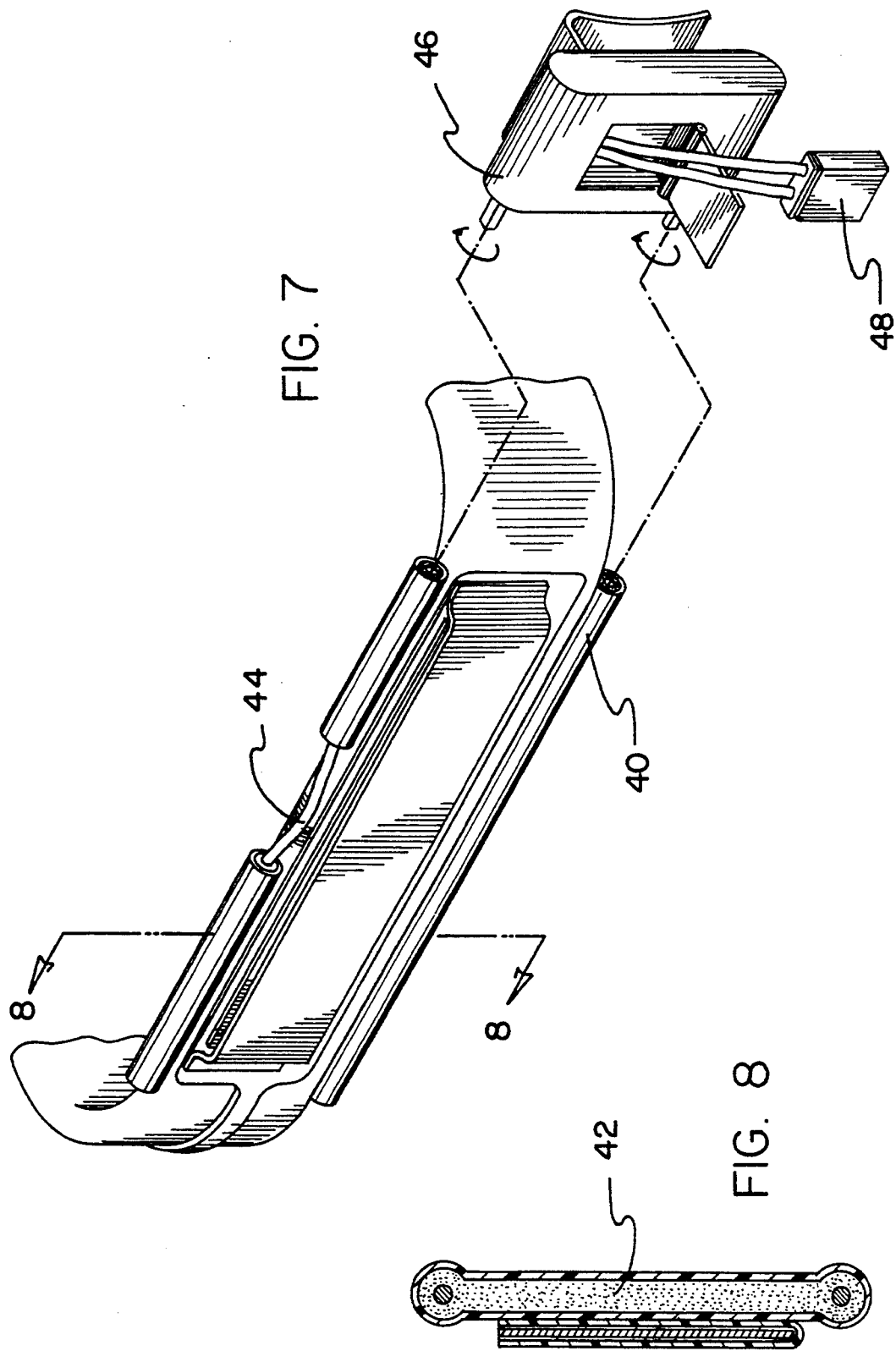

HEATED BACK SUPPORT

BACKGROUND OF THE INVENTION

1. Field of the Invention

The present invention relates to a heated back support and more particularly pertains to a device which may be used to provide heat to a user's back.

2. Description of the Prior Art

The use of devices which can be used to provide heat to a user's back are known in the prior art. More specifically, devices heretofore devised and utilized for the purpose of providing heat to a user's back are known to consist basically of familiar, expected and obvious structural configurations, notwithstanding the myriad of designs encompassed by the crowded prior art which have been developed for the fulfillment of countless objectives and requirements.

For example, U.S. Pat. No. 4,702,235 to Hong illustrates a device that supports the stomach with a cushioned and heated air chamber.

Other patents that illustrate components related to the present invention are U.S. Pat. No. 5,046,488 to Schiek, Sr.; U.S. Pat. No. 5,062,414 to Grim; U.S. Pat. No. 5,111,806 to Travis; and U.S. Pat. No. 5,147,261 to Smith et al.

While these devices fulfill their respective, particular objective and requirements, the aforementioned patents do not describe a heated back support that is simple and lightweight in construction and supports a user's back while simultaneously providing heat or massaging therapy thereto without using pneumatic mechanisms.

In this respect, the heated back support according to the present invention substantially departs from the conventional concepts and designs of the prior art, and in doing so provides an apparatus primarily developed for the purpose of providing heat to a user's back.

Therefore, it can be appreciated that there exists a continuing need for are an improved heated back support which can be used to provide heat to a user's back. In this regard, the present invention substantially fulfills this need.

SUMMARY OF THE INVENTION

In the view of the foregoing disadvantages inherent in the known types of devices for providing heat to a user's back now present in the prior art, the present invention provides an improved heated back support wherein the same can be utilized for providing heat to a user's back. As such, the general purpose of the present invention, which will be described subsequently in greater detail, is to provide a new and improved heated back support for providing heat to a user's back which has all the advantages of the prior art and none of the disadvantages.

To attain this, the present invention essentially comprises an elongated strap having a pile type fastener at one end and a complementary pile type fastener at the other end, the strap adapted to be worn around the midriff of a user's body, an upper heating element and a lower heating element coupled to the strap such that the upper heating element is positionable near a user's upper back region and the lower heating element is positionable near a user's lower back region, a pad coupled around the strap and heating elements, the pad adapted to radiate heat when the heating elements are energized and adapted to be positioned adjacent to a user's back, a power source coupled to the strap for energizing the heating elements, a power cable having a first end coupled to the heating element and a second end coupled to the power source, and a switch coupled to the power source and positionable in a first orientation to energize the upper heating element to heat a user's upper back region, positionable in a second orientation to energize the lower heating element to heat a user's lower back region, and positionable in a third orientation to energize both the upper and lower heating elements to heat a user's upper and lower back regions.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved heated back support which has all the advantages of the prior art and none of the disadvantages.

It is another object of the present invention to provide a new and improved heated back support which may be easily and efficiently manufactured and marketed.

It is a further object of the present invention to provide a new and improved heated back support which is of durable and reliable construction.

An even further object of the present invention is to provide a new and improved heated back support which is susceptible of a low cost of manufacture with regard to both materials and labor, and which accordingly is then susceptible of low prices of sale to the consuming public, thereby making such a heated back support economically available to the buying public.

Still yet another object of the present invention is to provide a new and improved heated back support which provides in the apparatuses and methods of the prior art some of the advantages thereof, while simultaneously overcoming some of the disadvantages normally associated therewith.

Still another object of the present invention is to provide a new and improved heated back support that is simple and lightweight in construction.

Yet another object of the present invention is to provide a new and improved heated back support that provides heating therapy to a user's back.

Yet another object of the present invention is to provide a new and improved heated back support that supports a user's back while simultaneously providing heat thereto.

Yet another object of the present invention is to provide a new and improved heated back support that braces, provides heat therapy, and provides massaging therapy to a user's back.

Even still another object of the present invention is to provide a heated back support comprising an elongated strap having a securement means at one end and a securable means at the other end, the strap adapted to be worn around a user's body, a plurality of heating elements coupled to the strap such that the elements are positionable adjacent to a user's back, a power source, and switch means coupled to the power source and heating elements for selectively energizing the elements to heat a user's back.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 7 is a side view of yet another alternate embodiment of the heated back support constructed in accordance with the principles of the present invention.

FIG. 8 is a side view of the heated back support taken along the line 8—8 of FIG. 7.

DESCRIPTION OF THE PREFERRED EMBODIMENT

Figure 1:
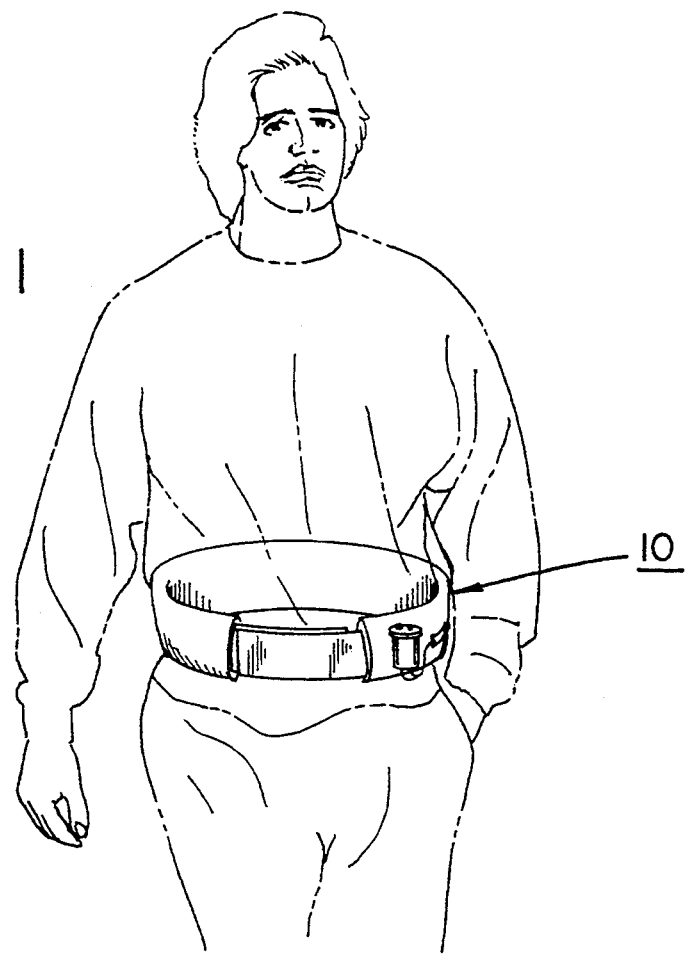
FIG. 1 is a perspective view of the heated back support constructed in accordance with the present invention in operation.
Figure 2:
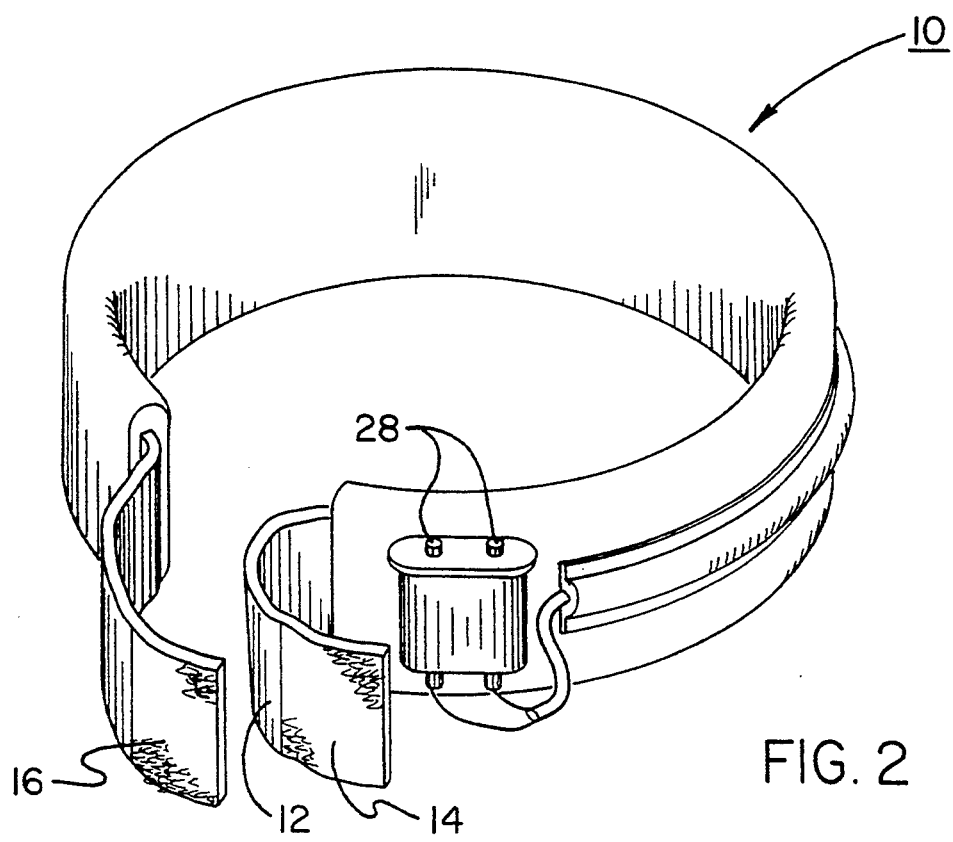
FIG. 2 is a perspective view of the heated back support constructed in accordance with the present invention.
Figure 4:
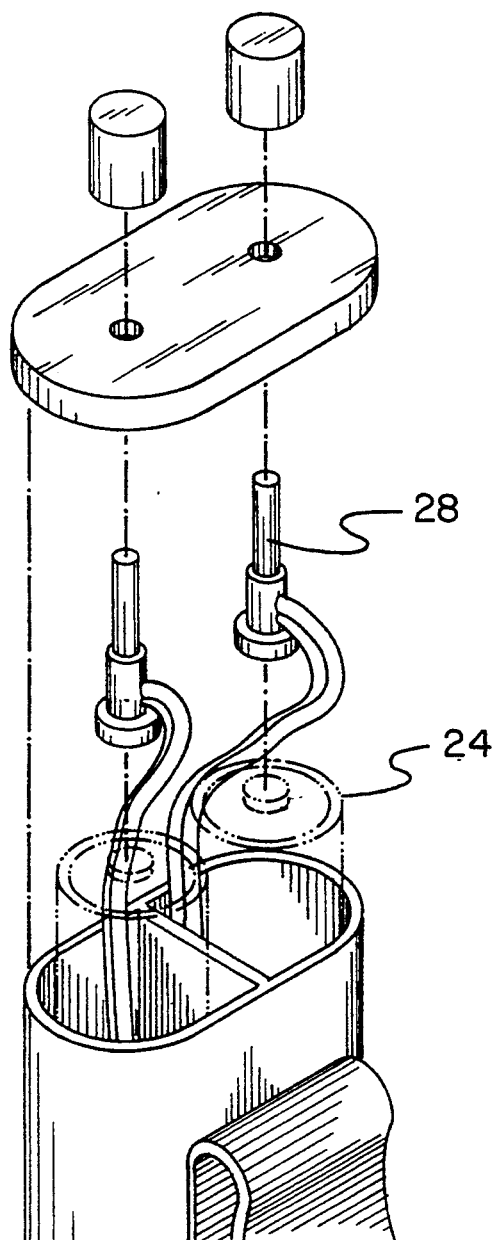
FIG. 4 is a schematic view of the switch, power supply, and heating elements of the present invention.
Figure 4:
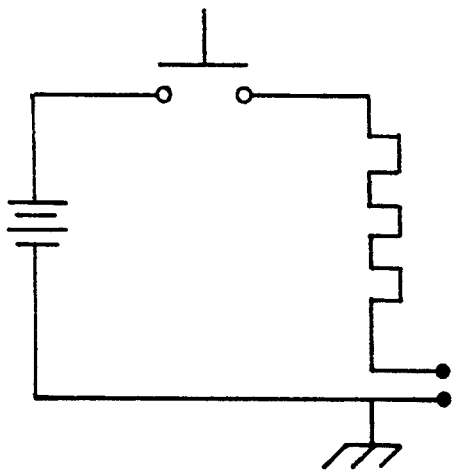
Figure 3:
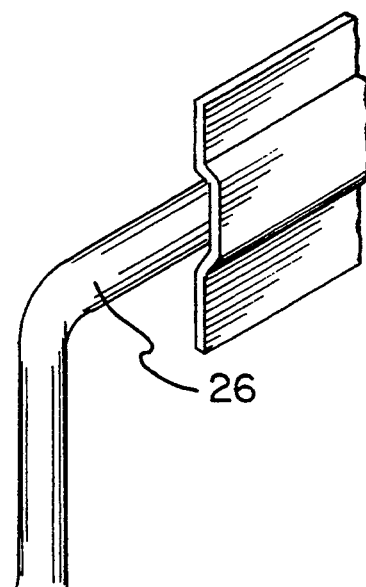
FIG. 3 is a close up view of the power source of the present invention.
Figure 5:
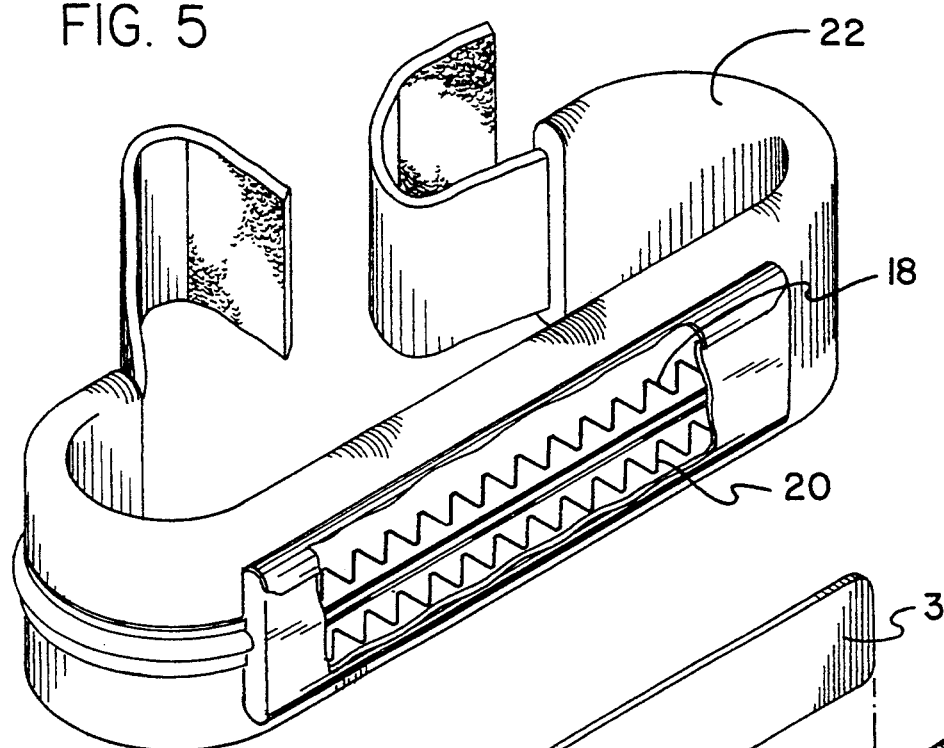
FIG. 5 is a perspective view of the heating elements of the present invention.

With reference now to the drawings, and in particular, to FIG. 1 through 8 thereof, a new and improved heated back support embodying the principles and concepts of the present invention and generally designated by the reference number 10 will be described.

As shown in FIGS. 1 through 5, the heated back support 10 comprises an elongated strap 12. The strap has a pile type fastener 14 at one end and a complementary pile type fastener 16 at the other end. The strap is adapted to be worn around the midriff of a user's body. An upper heating 18 element and a lower heating element 20 are coupled to the strap. The upper heating element is positionable near a user's upper back region. The lower heating element is positionable near a user's lower back region.

A pad 22 is coupled around the strap and heating elements. The pad is adapted to radiate heat when the heating elements are energized. The pad is adapted to be positioned adjacent to a user's back when the strap is secured about the midriff of a user's body.

A power source 24 is coupled to the strap for energizing the heating elements. A power cable 26 is coupled between the heating element and the power source.

Controls are provided through a power switch 28. The switch 28 is coupled to the power source and positionable in a first orientation to energize the upper heating element to heat a user's upper back region. The switch is also positionable in a second orientation to energize the lower heating element to heat a user's lower back region. The switch is also positionable in a third orientation to energize both the upper and lower heating elements to heat a user's upper and lower back regions.

Figure 6:
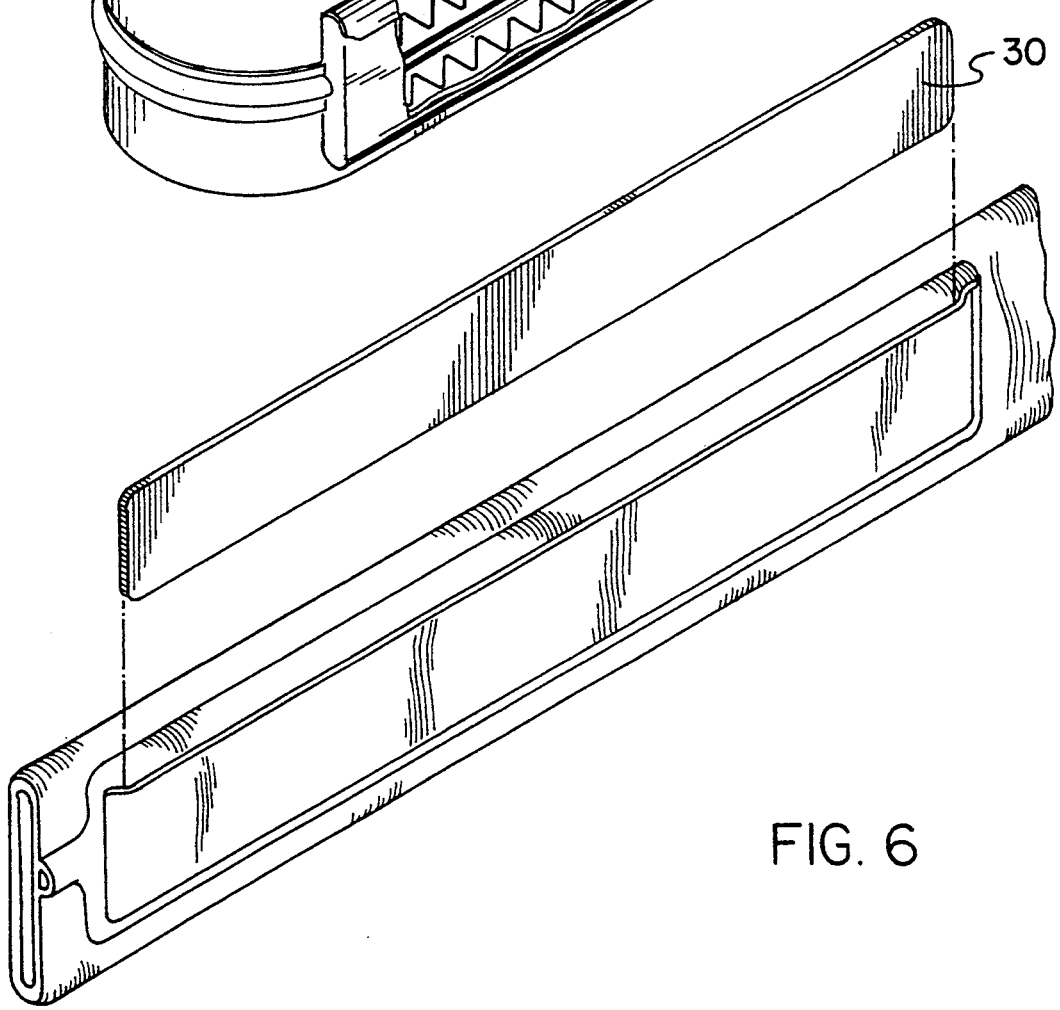
FIG. 6 is a perspective view of an alternate embodiment of the heated back support constructed in accordance with the principles of the present invention.

A second embodiment of the present invention is shown in FIG. 6. Such embodiment includes substantially all of the features of the first embodiment further including a rigid support plate 30 coupled to the strap to brace a user's back. Added physical support is provided through such strap.

A third embodiment of the present invention is shown in FIGS. 7 and 8. Such embodiment includes substantially all of the features of the first embodiment and second embodiment. It further includes a plurality of elongated and tubular housings 40 coupled to the strap 42. The housings are adapted to be positioned adjacent to a user's back. An elongated and rigid undulant wire 44 is disposed in each housing. A motor 46 is coupled to a each wire and the power source 48. When the motor is energized, it provides a torquing force to rotate the wire, whereby generating vibrations to massage a user's back.

The present invention is a back brace with a battery-powered heating element inside it. It can be worn either at home or on the job. The brace provides relief and comfort from back spasms for those who suffer more on cool or cold days, or who are simply more comfortable with a source of heat close to their backs.

The present invention consists of a wide belt that wraps around the midriff area of the user's body. Hook and loop material such as Velcro or something similar can be used to fasten the belt securely, yet enable quick removal. Inside the belt there are two sets of heating coils, one for the upper back area and one for the lower back. These two sets of heating coils are wired so that they can be controlled separately. This provides flexibility for the use—heat can be provided for the upper back only, the lower back only, or both the upper and lower back.

The brace of the present invention is powered by two standard D batteries. The battery pack can be clipped on to the user's belt or put in a pocket.

For those whose back problems are helped by heat, the brace of the present invention offers a promising solution to a nagging problem. Preliminary assessment indicates that this product can be manufactured from commonly available materials at a reasonable cost.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by LETTERS PATENT of the United States is as follows:

1. A heated back support comprising:
    an elongated strap having a pile type fastener at one end and a complementary pile type fastener at the other end, the strap adapted to be worn around the midriff of a user's body;
    an upper heating element and a lower heating element coupled to the strap such that the upper heating element is positionable near a user's upper back region and the lower heating element is positionable near a user's lower back region;
    a pad coupled around the strap and heating elements, the pad adapted to radiate heat when the heating elements are energized and adapted to be positioned adjacent to a user's back;
    a power source coupled to the strap for energizing the heating elements;
    a power cable coupled between the heating element and the power source; and
    a switch coupled to the power source and positionable in a first orientation to energize the upper heating element but not the lower heating element to heat a user's upper back region, positionable in a second orientation to energize the lower heating element but not the upper heating element to heat a user's lower back region, and positionable in a third orientation to energize both the upper and lower heating elements to heat a user's upper and lower back regions.

2. A vibrating heated back support comprising, in combination:
    an elongated strap having a pile type fastener at one end and a complementary pile type fastener at the other end, the strap adapted to be worn around the midriff of a user's body;
    an upper heating element and a lower heating element to the strap such that the upper heating element positioned near a user's back region and the lower heating element positioned near a user's lower back region;
    a plurality of elongated and tubular housings coupled to the strap, the housings adapted to be positioned adjacent to a user's back;
    a plurality of elongated and rigid undulant wires, each wire disposed in a housing;
    a pad coupled around the strap and heating elements, the pad adapted to radiate heat when the heating elements energize and adapted to be positioned adjacent a user's back;
    a power source coupled to the strap for energizing the heating elements;
    a power cable coupled between the heating element and the power source;
    a plurality of motors each motor coupled to a wire and the power source, the energized motor providing a torquing force to rotate the wire, thereby generating vibrations to massage a user's back;
    a switch coupled to the power source and positionable in a first orientation to energize the upper heating element to heat a user's upper back region, positionable in a second orientation to energize the lower heating element to heat a user's lower back region, and positionable in a third orientation to energize both the upper and lower heating elements to heat a user's upper and lower back regions and energize the plurality of motors to generate vibrations to massage a user's back.

* * * * *